United States Patent [19]
Hausheer et al.

[11] Patent Number: 6,031,006
[45] Date of Patent: Feb. 29, 2000

[54] METHOD OF TREATING DIABETIC NEPHROPATHY

[75] Inventors: Frederick H. Hausheer, Boerne; Aulma Parker; Seetharamulu Peddaiaghari, both of San Antonio, all of Tex.

[73] Assignee: BioNumerik Pharmaceuticals, Inc., San Antonio, Tex.

[21] Appl. No.: 09/422,486

[22] Filed: Oct. 21, 1999

[51] Int. Cl.[7] ................................................ A61K 31/10
[52] U.S. Cl. ............................................................. 514/711
[58] Field of Search ...................................... 514/706, 711

[56] References Cited

U.S. PATENT DOCUMENTS

| | | | |
|---|---|---|---|
| 5,661,188 | 8/1997 | Weissman et al. | 514/711 |
| 5,728,738 | 3/1998 | Engel et al. | 514/706 |
| 5,922,902 | 7/1999 | Haridas | 562/20 |

*Primary Examiner*—Raymond Henley, III
*Attorney, Agent, or Firm*—Thomas J. Dodd

[57] ABSTRACT

This invention relates to a method of treating patients afflicted with diabetic nephropathy. The method includes administering to a patient in need of treatment an effective amount of a thiol or reducible disulfide compound according to the formula set forth in the specification.

4 Claims, No Drawings

METHOD OF TREATING DIABETIC NEPHROPATHY

FIELD OF THE INVENTION

This invention relates to a method for preventing and/or treating a patient suffering from diabetic nephropathy. The method involves administering an effective amount of a disulfide or thiol-containing compound to a patient suffering from an ischemic condition.

BACKGROUND OF THE INVENTION

One of the most common complications of diabetes is nephropathy. Diabetic nephropathy is thought to be caused by the progressive glycosylation of proteins, leading to a progressive loss of renal function. Diabetic nephropathy generally results in a chronic and progressive degradation of kidney function, to the point where the patient must undergo dialysis or transplant to survive. Diabetic nephropathy is believed responsible for at least 25% of all renal dialysis patients, with an increase in morbidity and costs of medical care.

Current therapies are ineffective to prevent or reduce the onset of diabetic nephropathy. The current popular treatment involves the administration of angiotensin converting enzyme (ACE) inhibitors such as captopril, to patients with chronic nephropathy as a result of diabetes. Calcium channel blockers have also been administered for this purpose, and a high protein diet has also been suggested to slow the onset of nephropathy. It has been suggested that the only true way to prevent diabetic nephropathy (and other diabetic complications) is through strict glycemic control.

Aldose reductase (AR) inhibitors have been tested in humans, mainly in the 1980s, with the hope that these agents would slow the progress of diabetic retinopathy, a condition that often led to blindness. The AR inhibitors (alrestatin and sorbinil were two AR inhibitors that were clinically tested) showed some efficacy, but were not well tolerated by patients. No AR inhibitor to date has been approved for use in the United States for diabetic nephropathy or any other indication.

Mesna (sodium 2-mercaptoethene sulfonate) and dimesna (disodium 2,2'-dithiobis ethane sulfonate) are known therapeutic compounds, which have heretofore demonstrated a wide variety of therapeutic uses. Both mesna and dimesna have been shown to be effective protective agents against certain specific types of toxicity associated with the administration of cytotoxic drugs used to treat patients for various types of cancer. In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses that can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The structures of both mesna and dimesna are shown below as Formula a and Formula b respectively.

   (a)

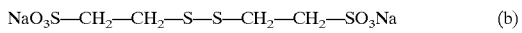   (b)

As is well known, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, intracellular spaces, intestines, and others, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with cisplatin, carboplatin, and taxane derivatives.

Mesna and dimesna, as well as some analogues of these compounds, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 15 g/m$^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

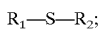

wherein:

$R_1$ is hydrogen, X-lower alkyl, or X-lower alkyl-$R_3$;
$R_2$ is -lower alkyl-$R_4$;
$R_3$ and $R_4$ are each individually $SO_3M$ or $PO_3M_2$;
X is absent or X is sulfur; and M is an alkali metal.

The process involves a two step single pot synthetic process, which results in the conversion of an alkenyl sulfonate salt or acid to the desired formula I compound. The process in the case of mesna is a single step process, which converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of compounds of formula I, below, for treating patients prone to develop diabetic nephropathy and for treating those already suffering from that condition.

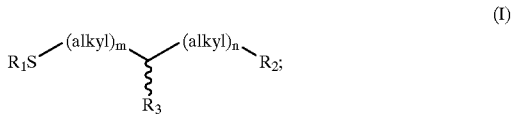

(I)

wherein:

$R_1$ is hydrogen, lower alkyl or

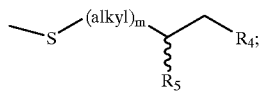

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

Effective amounts of the formula I compounds to be administered according to the method of this invention vary, and depend on the severity of the patient's distress.

Accordingly, it is an object of this invention to provide for a method of safely and effectively treating and/or preventing the onset of diabetic nephropathy.

Another object is to provide a method of treating diabetic nephropathy by administration of a thiol or reducible disulfide to the patient in need of treatment.

Other objects will become apparent upon a reading of the following description.

DESCRIPTION OF THE PREFERRED EMBODIMENTS

The preferred embodiments herein described are not intended to be exhaustive nor to limit the invention to the precise form disclosed. They are chosen and described to explain the principles of the invention, and its application and practical use to best enable others skilled in the art to follow its teachings.

The method of this invention involves the administration of an effective amount of a formula I compound to a patient suffering from diabetic nephropathy. Administration may be either oral or parenteral.

The effective amount of the formula I compound will necessarily depend upon the severity of the patient's condition. Since the formula I compounds are essentially non-toxic (over 40 g/m² have been intravenously administered in a single dose to human patients with no adverse effects), large amounts can be safely administered. The preferred dosage to treat diabetic nephropathy may be as low as 0.1 mg/kg up to 1,000 mg/kg. The more severe the condition, the greater the amount and/or frequency of dose of the formula I compound should be administered to provide an effective response.

The following examples illustrate the efficacy of the formula I compounds in inhibiting AR.

EXAMPLE 1

Aldose reductase assays were as described in Nishimura C., Yamaoka T., Mizutani M., Yamashita K., Akera T., Tanimoto T., Purification And Characterization Of The Recombinant Human Aldose Reductase Expressed In Baculovirus System, Biochem. Biophys. Acta, Jun. 24, 1991; 1078(2):171–8.

Briefly, Dimesna (0–20 μM) was incubated at 37° C. with aldose reductase (0.0016 units, human recombinant, expressed in SF 9 cells) and NADPH (0.15 mM) in sodium phosphate buffer (100 mM, pH 6.2). To initiate assays, glucose (10–150 mM) was added to reactions and the decrease in absorbance at 340 nm (oxidation of NADPH) was monitored. Assays were run in duplicate or triplicate. Slopes were calculated using Varian-Cary software package 2.0 and averaged. In all cases errors were 4% or less. Lineweaver Burk analysis (Enzyme Kinetics, version 1.61) was used to calculate inhibition constants.

EXAMPLE 2

Aldose reductase assays were as described above. Dimesna (0–30 mM) was evaluated for its effect on the NADPH dependent reduction of glyceraldehyde (0.050–6 mM) to aldose at 37° C. Assays were run in duplicate or triplicate. Slopes were calculated using Varian-Cary software package 2.0 and averaged. In all cases errors were 4% or less. Lineweaver Burk analysis (Enzyme Kinetics, version 1.61) was used to calculate inhibition constants.

As shown in the above tables, Dimesna inhibits aldose reductase catalyzed reduction of glucose to sorbitol and glyceraldehyde to aldose with $K_i$ values of 32 and 15.5 μM, respectively. Lineweaver Burk plots of the data are nearly parallel and, thus, support an uncompetitive inhibition of the aldose reductase reaction by Dimesna. These data suggest that Dimesna binds to some form of an enzyme substrate complex. Aldose reductase is a multisubstrate enzyme requiring both NADPH and an aldose sugar for turnover. Dimesna binding may be reversible or irreversible.

Administration is preferably through parenteral or oral routes. For parenteral administration, the formula I compound is dissolved in a suitable solvent, most preferably water, to produce a solution that may be injected or infused. One or more pharmaceutically acceptable excipients may also be added to provide for an elegant formulation as defined in the art.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a swallowable container such as a gelatin capsule or the like.

Administration of the formula I compound should be made as soon as possible following a test confirming the diagnosis of diabetic nephropathy. Preferred initial dose is between 20 mg/kg and 500 mg/kg. Careful observation and blood analysis is performed regularly after diagnosis as per accepted medical procedures for treating diabetic nephropathy.

For prophylactic dosing of patients with diabetes who are judged likely to develop diabetic nephropathy, daily dosing with the formula I compound is preferred, with the preferred daily dose being split into several spaced individual doses. Preferred amounts range from 20 mg/day up to 2 g/day.

Other accepted methods of treatment, such as co-administration of ACE inhibitors or recommending a high protein diet, may also be combined with the administration of the formula I compound. Due to the excellent safety profile, additional doses of the formula I compound may be administered safely if the initial dose does not produce a response.

It is understood that the above description is in no way limiting of the invention, which may be modified within the scope of the following claims.

What is claimed is:

1. A method of treating a patient afflicted with diabetic nephropathy, said method comprising administering an effective amount of a compound of formula I:

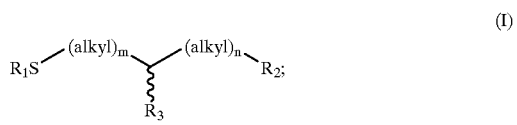
(I)

wherein:

$R_1$ is hydrogen, lower alkyl or

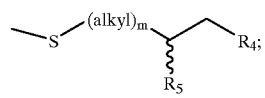

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 2,000 mg/kg of body weight.

3. The method of claim 1 wherein the compound is administered orally.

4. The method of claim 1 wherein the compound is administered parenterally.

* * * * *